(12) United States Patent
Marsden

(10) Patent No.: US 6,869,405 B2
(45) Date of Patent: Mar. 22, 2005

(54) BLUNT CANNULA AND FILTER ASSEMBLY AND METHOD OF USE WITH POINT-OF-CARE TESTING CARTRIDGE

(75) Inventor: Stewart Marsden, Montville, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 187 days.

(21) Appl. No.: 10/109,300

(22) Filed: Mar. 27, 2002

(65) Prior Publication Data

US 2002/0143298 A1 Oct. 3, 2002

Related U.S. Application Data

(60) Provisional application No. 60/280,436, filed on Mar. 30, 2001, and provisional application No. 60/280,401, filed on Mar. 30, 2001.

(51) Int. Cl.[7] .............................. A61B 5/00; B65D 81/00
(52) U.S. Cl. ..................................................... 600/573
(58) Field of Search ................................. 600/573, 576, 600/577, 578; 210/645; 422/61, 68.1, 99–102; 206/305, 569; 604/264, 266, 272, 523

(56) References Cited

U.S. PATENT DOCUMENTS

| | | |
|---|---|---|
| 3,593,854 A | 7/1971 | Swank |
| 4,116,845 A | 9/1978 | Swank |
| 4,477,575 A | 10/1984 | Vogel et al. |
| 4,619,639 A | 10/1986 | Nose et al. |
| 4,810,394 A | 3/1989 | Masuda |
| 5,096,669 A | 3/1992 | Lauks et al. |
| 5,139,685 A | 8/1992 | de Castro et al. |
| 5,219,529 A * | 6/1993 | Ngo et al. .................. 422/101 |
| 5,423,989 A | 6/1995 | Allen et al. |
| 5,460,777 A | 10/1995 | Kitajima et al. |
| 5,638,828 A | 6/1997 | Lauks et al. |
| 5,653,243 A | 8/1997 | Lauks et al. |
| 5,779,650 A | 7/1998 | Lauks et al. |
| 5,849,505 A | 12/1998 | Guirguis |
| 5,964,785 A | 10/1999 | Desecki et al. |
| 6,045,699 A | 4/2000 | Yazawa et al. |

FOREIGN PATENT DOCUMENTS

| | | |
|---|---|---|
| EP | 0 550 950 A2 | 7/1993 |
| EP | 0 743 095 A1 | 11/1996 |
| EP | 0 826 412 A2 | 3/1998 |
| EP | 0 896 826 A1 | 2/1999 |
| WO | WO 99/39298 | 8/1999 |

* cited by examiner

Primary Examiner—Max F. Hindenburg
Assistant Examiner—Brian Szmal

(57) ABSTRACT

A kit includes a point-of-care testing cartridge and a blunt cannula assembly. The blunt cannula assembly includes a blunt cannula that has a filter therein for filtering cellular components from whole blood and enabling plasma to be delivered by the blunt cannula to the testing cartridge.

7 Claims, 10 Drawing Sheets

BLUNT CANNULA AND FILTER ASSEMBLY AND METHOD OF USE WITH POINT-OF-CARE TESTING CARTRIDGE

RELATED APPLICATIONS

This application claims priority on U.S. Provisional Patent Appl. No. 60/280,436 and U.S. Provisional Patent Appl. No. 60/280,401 both of which were filed on Mar. 30, 2001.

BACKGROUND OF THE INVENTION

1. Field of the Invention

The subject invention relates to a blunt cannula with a filter material disposed therein for separating constituent parts of a bodily fluid, such as blood. The invention also relates to a kit of parts that includes a point-of-care testing cartridge and a blunt cannula that has an internal filter and to a method of using such a blunt cannula and filter with a point-of-care testing cartridge.

2. Description of the Related Art

Many medical procedures require diagnostic tests to be performed on a sample of bodily fluid. Some such tests require the bodily fluid to be separated into its constituent parts. For example, plasma is the fluid part of blood. Some diagnostic tests require the plasma, with its clotting mechanisms in tact, to be separated from more solid components of blood.

The prior art includes arrangements of glass fibers within instrumentation and filter devices for separating plasma from blood. Such systems are shown, for example, in U.S. Pat. No. 4,619,639, U.S. Pat. No. 4,810,394 and U.S. Pat. No. 5,460,777. Other materials are used for filtration in blood bags, test strips, card analysis systems and in-line filter systems.

Blood and other bodily fluids typically are analyzed in a laboratory remote from the patient. However, point-of-care testing systems have been developed recently. The prior art point-of-care testing system includes a portable clinical analyzer and testing cartridges. The testing cartridge comprises a small housing with an internal reservoir for receiving a small volume of blood, typically in the range of 65 µl and 110 µl. The testing cartridge further includes an inlet port that communicates with the internal reservoir and a plurality of contact pads and sensors. Blood can be collected in a conventional prior art syringe and then injected from the syringe into the inlet port of the testing cartridge. The contact pads and sensors of the testing cartridge then are engaged in a receptacle of the portable clinical analyzer. The analyzer performs certain diagnostic tests and provides a point-of-care read out of the test results. The portable clinical analyzer can be used with a printer to provide a printed output and with an interface to provide communication with a central data station that will store and appropriately utilize the test results. Examples of point-of-care test systems, as described above, are provided by i-STAT Corporation, Diametrics Medical, Inc. and AVL Scientific Corporation.

Point-of-care testing cartridges primarily receive anticoagulated whole blood for analysis. This may require the cartridge to separate the cellular components of blood, as in the Abbott Vision System. Alternatively, the cartridge may use sensors for direct measurement of the analytes, such as in the Abbott i-STAT system.

Point-of-care testing systems offer many efficiencies over laboratory analysis. However, it is difficult to transfer blood accurately from the syringe to the testing cartridge. More particularly, it is unsafe and/or undesirable to use a contaminated sharply pointed metallic needle cannula while manipulating the very small testing cartridge. Thus, it is preferable to manually disengage the used needle cannula from the syringe. The user then must attempt to guide the short and relatively wide Luer tip of the syringe to the small inlet port of the testing cartridge. Significant risk exists for missing the inlet port and losing at least a portion of the blood that had been collected. This stray blood creates the risk for contamination and may leave an insufficient volume of blood to complete the diagnostic tests. Thus, the healthcare technician may have to perform another inconvenient and painful drawing of blood from the patient. Furthermore, the partly filled testing cartridge may have to be discarded, thereby increasing costs associated with a fairly simple diagnostic test.

Plastic cannulas are a suitable substitute for sharply pointed metallic cannulas in many situations, including those situations where a cannula must pierce a septum or where a connection with an IV fitting is appropriate. The prior art plastic cannula is unitarily molded from plastic and includes a proximal end, a distal end and a lumen extending between the ends. The lumen is widely open and tapered at the proximal end of the plastic cannula and is configured for fluid-tight frictional engagement over the tapered tip of a typical Luer fitting. The proximal end of a plastic cannula may further includes diametrically opposite projections that are dimensioned and configured for engagement with the threads of a Luer collar.

The distal end of the prior art plastic cannula includes a narrow cylindrical wall that surrounds the lumen through the cannula. The narrow cylindrical wall may be conically tapered to define a fairly blunt tip. However, some prior art plastic cannulas have a distal tip that is sufficiently sharp to pierce a rubber septum. In this regard, the sharpness of the distal tip normally would be limited by the diameter of the lumen through the cannula. This would result in a fairly blunt tip that might not be able to pierce through many septums. However, plastic cannulas have been developed with diametrically opposite triangular extension of the tubular sidewall at the extreme distal end of the plastic cannula. These triangular extensions converge and meet at a well defined point at the extreme distal end of the plastic cannula. A pair of identical side ports open transversely at the distal end and at locations between these converging triangular extensions. A plastic cannula of this type often is used to deliver a drug intravenously through the septum on an IV fitting. Although the blunt cannula is sufficiently sharp to pierce a septum, it will not accidentally stick a patient.

It is an object of the subject invention to provide a convenient way for separating plasma from blood and efficiently delivering the plasma to a point-of-care testing cartridge for analysis.

SUMMARY OF THE INVENTION

The subject invention is directed to a kit that comprises a point-of-care testing cartridge and a blunt cannula with a filter material secured therein.

The blunt cannula may be structurally similar to prior art blunt cannulas or plastic fittings sold by Becton Dickinson under the trademark INTERLINK®. More particularly, the blunt cannula includes opposite proximal and distal ends and a lumen extending between the ends. The proximal end of the blunt cannula includes a tapered entry to the lumen that is dimensioned for fluid-tight engagement over the tapered Luer tip of a syringe. The proximal end of the blunt cannula may further include diametrically opposite projections that are dimensioned for threaded engagement with a Luer collar.

Distal portions of the blunt cannula include a narrow cylindrical tube with an outside diameter significantly less than the outside diameter at the distal end of a tapered Luer tip. The cylindrical tube tapers to a blunt distal end. The blunt end may define a conical or toroidal taper with a single axial opening to the lumen at the extreme distal end of the blunt cannula. Alternatively, the distal end of the blunt cannula may include diametrically opposite triangular projections that converge toward one another. The triangular projections may meet at a point sufficiently sharp to pierce a rubber septum. The triangular projections of the blunt cannula may be separated from one another by side ports that open transversely at the distal end of the cannula.

The blunt cannula of the subject invention differs from prior art blunt cannulas by the incorporation of a filter in the blunt cannula. The filter communicates with the lumen, and may be disposed at the distal end of the tapered proximal entry to the lumen. The filter material may be selected to separate plasma from the cellular components of blood. The filter material may be formed as one piece or as a plurality of adjacent layers that are secured either mechanically or chemically. The layers may comprise both low density material and high density material selected to achieve effective separation of the plasma. For example, the layers of the filter material may comprise glass fibers, Orlon, glass wool, Dacron, nylon or ceramic fibers. The materials are selected to produce a graduated outcome leading to separation of the cellular components, including red blood cells, white blood cells and platelets from whole blood, thereby leaving a plasma fluid for analysis.

The point-of-care testing cartridge may be of conventional prior art design, as described above. Alternatively, the point-of-care testing cartridge may be of a new design that is particularly adapted for analysis of the plasma that can be separated from the whole blood by the filter in the blunt cannula of the subject invention.

The kit of the subject invention may be used with a syringe. The syringe may be employed to collect a sample of blood or other bodily fluid that will be filtered and then analyzed. The collection of the blood or other bodily fluid in the syringe may be carried out in a conventional manner employing a metallic needle cannula for direct access to a blood vessel. Alternatively, blood may be collected with a blood collection set that has a fitting to which the syringe is mated. Still further, a plastic fitting may be mounted directly to the distal end of the syringe and may be placed in communication with an IV line for drawing a sample of blood or other bodily fluid.

The blunt cannula of the kit is mounted to the syringe after the blood or other fluid has been collected. The distal end of the blunt cannula then is mounted in the entry port of the testing cartridge of the kit. The plunger of the syringe assembly then is moved distally in the syringe body to urge blood or other fluid into the filter. The filter retains cellular components of the blood, but permits liquid components to pass into the testing cartridge for analysis.

The subject invention also is directed to a method for obtaining and analyzing plasma. The method may comprise a first step of employing a syringe to obtain a sample of blood from a patient. This first step may further comprise mounting a metallic needle cannula to the Luer tip of a syringe and then directly accessing a blood vessel of a patient. Alternatively, the first step may comprise mounting a plastic fitting to the syringe and accessing a fitting of a blood collection set or an IV line. The blood collection set or IV line also could be accessed directly by the syringe. The method next comprises a step of providing a blunt cannula with filter material therein and mounting the blunt cannula to the syringe such that the filter material communicates with the passage through the Luer tip of the syringe. The method proceeds by placing the distal end of the blunt cannula into the entry port of a point-of-care testing cartridge. The plunger of the syringe then is urged distally relative to the syringe body. As a result, the whole blood in the fluid receiving chamber of the syringe is urged into the filter of the blunt cannula. The filter retains cellular components of blood, but passes plasma through the lumen of the blunt cannula and into the entry port of the testing cartridge. The syringe and the blunt cannula then can be separated from the testing cartridge. The entry port to the testing cartridge then may be closed, and the sensors of the testing cartridge may be placed in communication with a portable clinical analyzer for analysis of the plasma in the reservoir of the testing cartridge.

DETAILED DESCRIPTION

Figure 1:
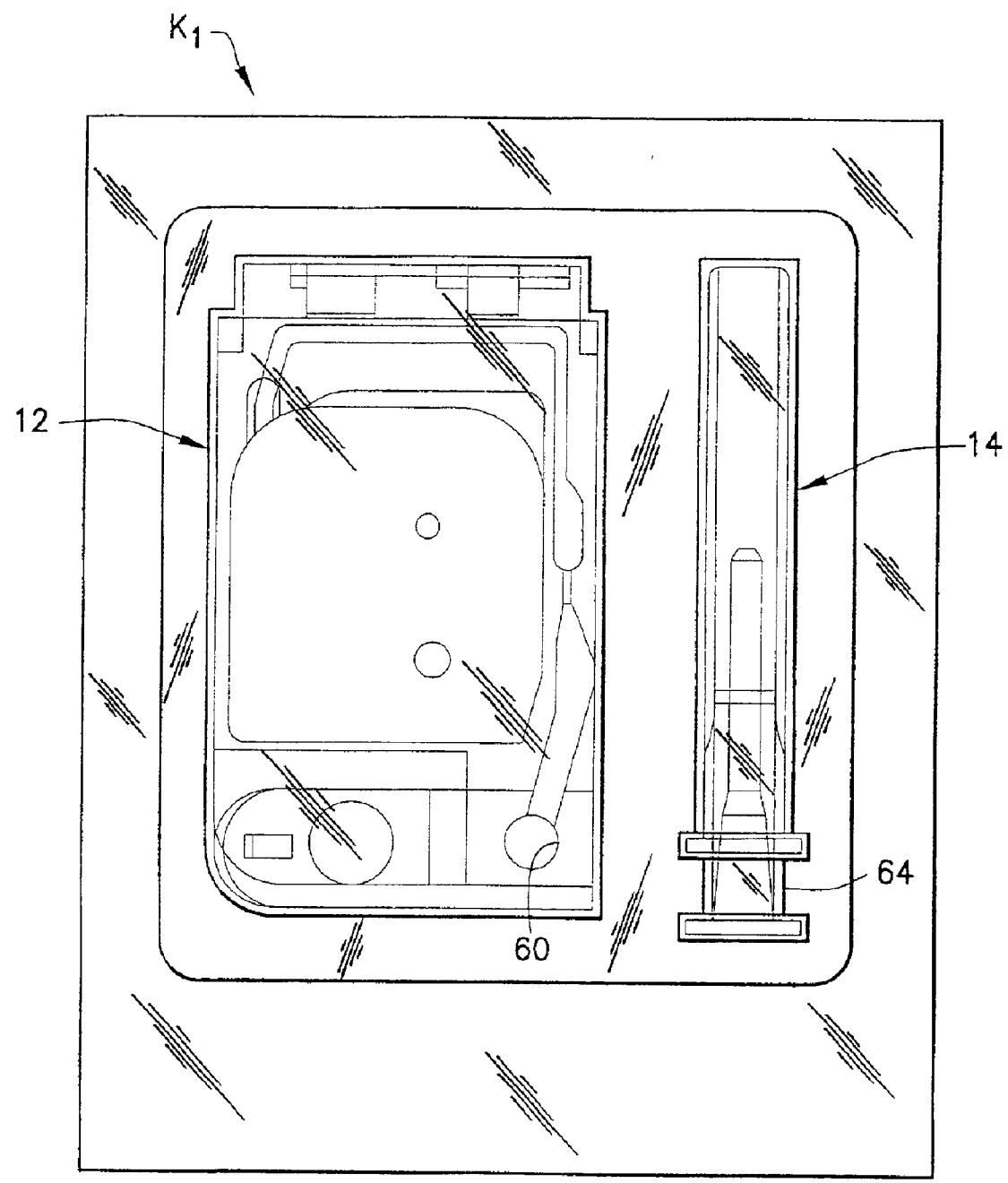
FIG. 1 is a top plan view of a first embodiment of a kit in accordance with the subject invention.

A kit in accordance with the subject invention is identified as $K_1$ in FIG. 1. Kit $K_1$ includes a point-of-care testing cartridge 12, as shown in FIG. 3, and a blunt cannula assembly 14, as shown in FIG. 4.

Figure 2:
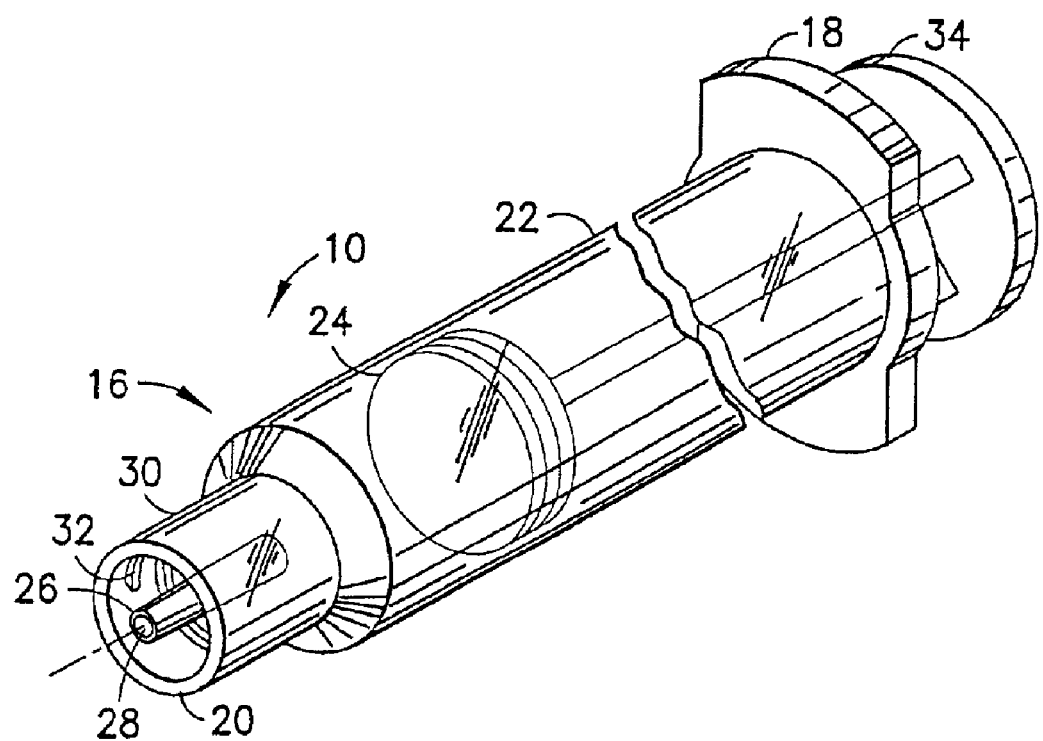
FIG. 2 is a perspective view of a syringe for use with the kit of FIG. 1.

Kit $K_1$ is used with a syringe assembly 10, as shown in FIG. 2. Syringe assembly 10, as shown in FIG. 2, includes a syringe body 16 having a proximal end 18 and a distal end 20. A barrel 22 extends distally from proximal end 18 and defines a cylindrical fluid receiving chamber 24 that is widely open at proximal end 18. A frustoconically tapered tip 26 extends from barrel 22 to distal end 20 of syringe body 16. Tip 26 is provided with a narrow cylindrical passage 28 that communicates with fluid receiving chamber 24 of barrel 22. A Luer collar 30 projects distally from barrel 22 and concentrically surrounds tip 26. Luer collar 30 is provided with an internal array of threads 32. Syringe assembly 10 further includes a plunger 34 slideably disposed in fluid receiving chamber 24 and in fluid-tight engagement with the cylindrical walls of chamber 22. Plunger 34 can be moved alternately in proximal or distal directions for urging fluid through passage 28 in tip 26 and into or out of fluid receiving chamber 24.

Figure 3:
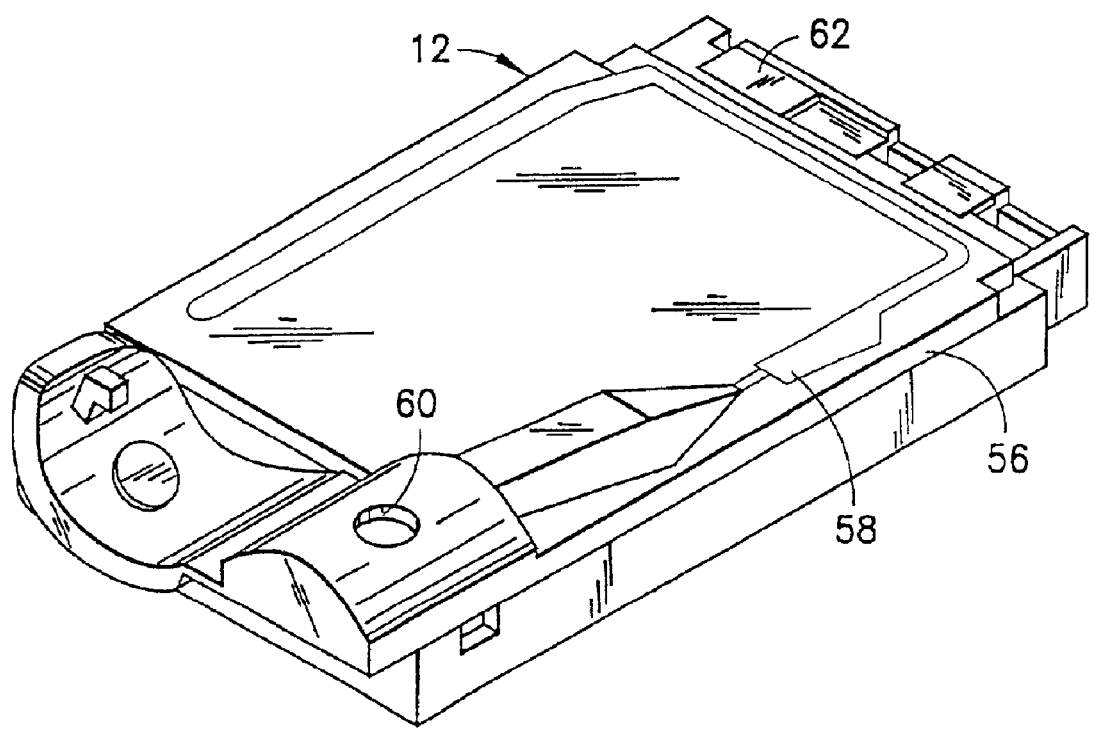
FIG. 3 is a perspective view of the testing cartridge of the kit of FIG. 1.
Figure 4:
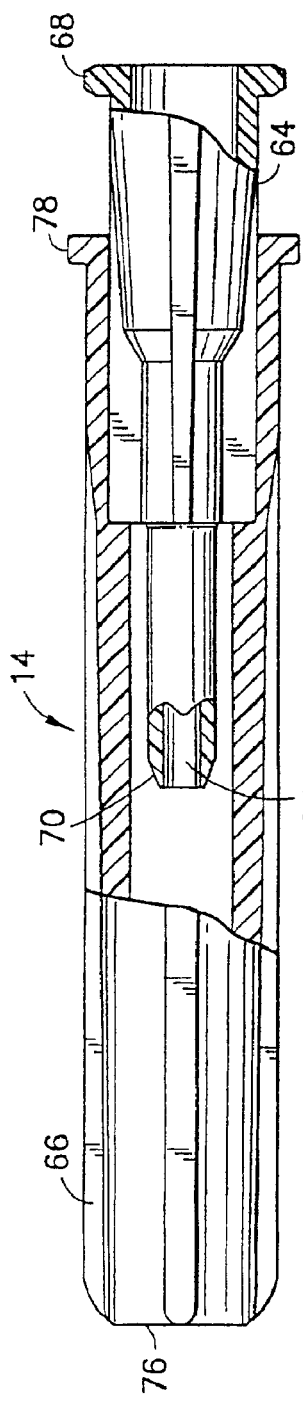
FIG. 4 is a side elevational view, partly in section, of the blunt cannula assembly of the kit in FIG. 1.

Point-of-care testing cartridge 12 of kit $K_1$ is shown in FIG. 3 and may be of any of several prior art designs, including those manufactured by i-STAT Corporation, Diametrics Medical, Inc., AVL Scientific Corporation or any other such testing cartridges that are available or become available. One such testing cartridge is disclosed in U.S. Pat. No. 5,638,828, the disclosure of which is incorporated herein by reference.

Testing cartridge 12 includes a generally rectangular body 56 with a length of approximately 1.5–2.0", a width of about 1.0" and a thickness of about 0.25". A fluid reservoir 58 is formed inside body 56 of cartridge 12 and has a volume in the range of 65 $\mu$l and 110 $\mu$l. Body 56 further includes an entry port 60 that communicates with reservoir 58. Entry port 60 is slightly tapered from a relatively large diameter portion externally on housing 56 to a relatively smaller cross-section closer to reservoir 58. Testing cartridge 12 further includes contact pads and sensors 62 that can be placed in communication with a portable clinical analyzer for performing various point-of-care diagnostic tests on the sample of blood in the reservoir 58 and for providing various readout data that can be used by a health care technician at the point-of-care and/or at a remote location.

Figure 5:
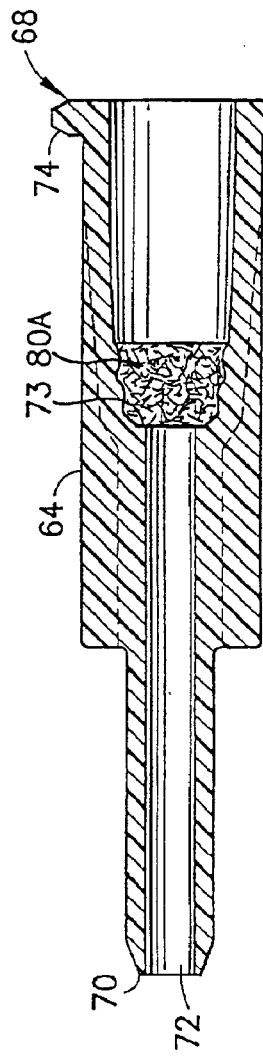
FIG. 5 is a longitudinal cross-sectional view of the blunt cannula shown in FIG. 4.
Figure 6:
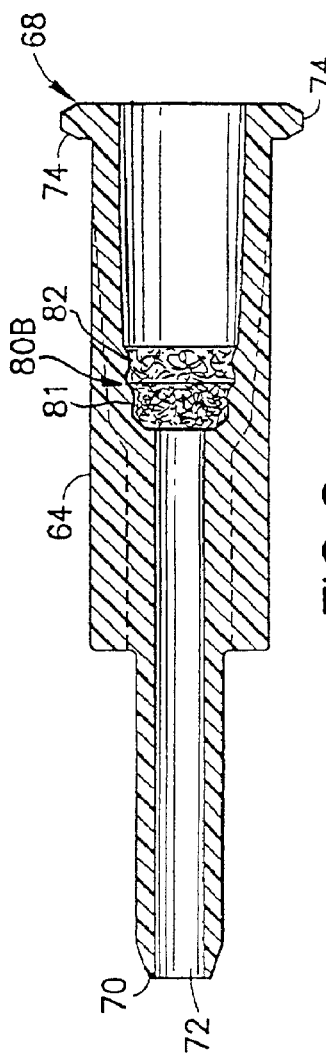
FIG. 6 is a longitudinal cross-sectional view similar to FIG. 5, but showing an alternate filter in the blunt cannula.

Blunt cannula assembly 14 of kit $K_1$ is illustrated more clearly in FIGS. 4–6. Blunt cannula assembly 14 includes a blunt cannula 64 that may be of the type sold by Becton Dickinson under the trademark INTERLINK®. As shown more clearly in FIG. 5, the blunt cannula 64 is unitarily molded from a plastic material and includes a proximal end 68 and a distal end 70 to define a length of slightly over 1.0". A lumen 72 extends between ends 68 and 70. Portions of lumen 72 adjacent proximal end 68 define a tapered entry that substantially conforms to the size and shape of the tapered passage in hub 46 of needle assembly 36. Thus, the tapered entry to lumen 72 at proximal end 68 of blunt cannula 64 can provide a fluid-tight frictional engagement with tapered tip 26 of syringe body 16. Portions of lumen 72 adjacent proximal end 68 define a maximum inside diameter of approximately 0.169". A step 73 is defined at the distal end of the tapered proximal entry to lumen 72. Lumen 72 continues distally from step 73 at a constant inside diameter of about 0.054 inch. Proximal end 68 of blunt cannula 64 is characterized further by a pair of diametrically opposite lugs 74 that are dimensioned and configured for engagement with internal threads 32 of Luer collar 30. Thus, lugs 74 can be engaged threadedly with Luer collar 30 for urging the tapered proximal open end of lumen 72 into fluid-tight frictional engagement with tapered distal tip 26 of syringe body 16. In other embodiments, the syringe may not have a Luer collar, and blunt cannula 64 can merely be moved axially into fluid-tight frictional engagement over distal tip 26.

Portions of blunt cannula 64 adjacent distal end 70 define a frustoconical taper having a minimum outside diameter of approximately 0.072" at distal end 70 to a maximum outside diameter 0.10" at a location spaced from distal end 70 by a distance of about 0.045". Blunt cannula 64 continues at a substantially constant outside diameter of approximately 0.10" to a location spaced approximately 0.40" from distal end 70. Both the minimum outside diameter at distal end 70 and the maximum outside diameter of 0.10" at locations adjacent the frustoconical taper are substantially less than corresponding dimensions of distal tip 26 of syringe body 16. Furthermore, the degree of taper at distal end 70 of blunt cannula 64 is greater than the taper existing on tip 26 of syringe body 16.

Returning to FIG. 4, safety shield 66 of blunt cannula assembly 14 includes a closed distal end 76 and an open proximal end 78. Proximal end 78 of safety shield 66 can be telescoped over distal end 70 of blunt cannula 64 and can be engaged frictionally with portions of blunt cannula 64 between proximal and distal ends 68 and 70.

Blunt cannula 64, as shown in FIG. 5, is provided with a filter 80A adjacent step 73 between the cross-sectionally large and small portions of lumen 72. Filter 80A preferably is formed from glass fibers (borosilicate), Orlon, glass wool, Dacron, nylon or ceramic fibers with a pore size of 0.2–5.0 microns. Filter 80A separates at least certain cellular components of the whole blood, thereby allowing plasma to pass through filter 80A. Additionally, filter 80A may be treated with or include an anticoagulant such as heparin to postpone or prevent clotting of plasma that passes through filter 80A.

FIG. 6. shows a blunt cannula 64 with a dual-layer filter 80B having a first filter layer 81 and a second filter layer 82 that may be mechanically or chemically joined. Filter layers 81 and 82 may be selected from two of the optional materials identified for the filter 80A. However, the combination of filters is selected for producing a graduated outcome leading to complete separation of the cellular components and providing plasma fluid for analysis.

Filter 80B should be structurally similar to filter 80A, and hence includes a pore size in the range of 0.2–5 microns. Additionally, the material preferably has a low and high density range (0.5–0.13 g/cm) for low density and a nominal 0.14 g/cm high density respectively.

Figure 7:
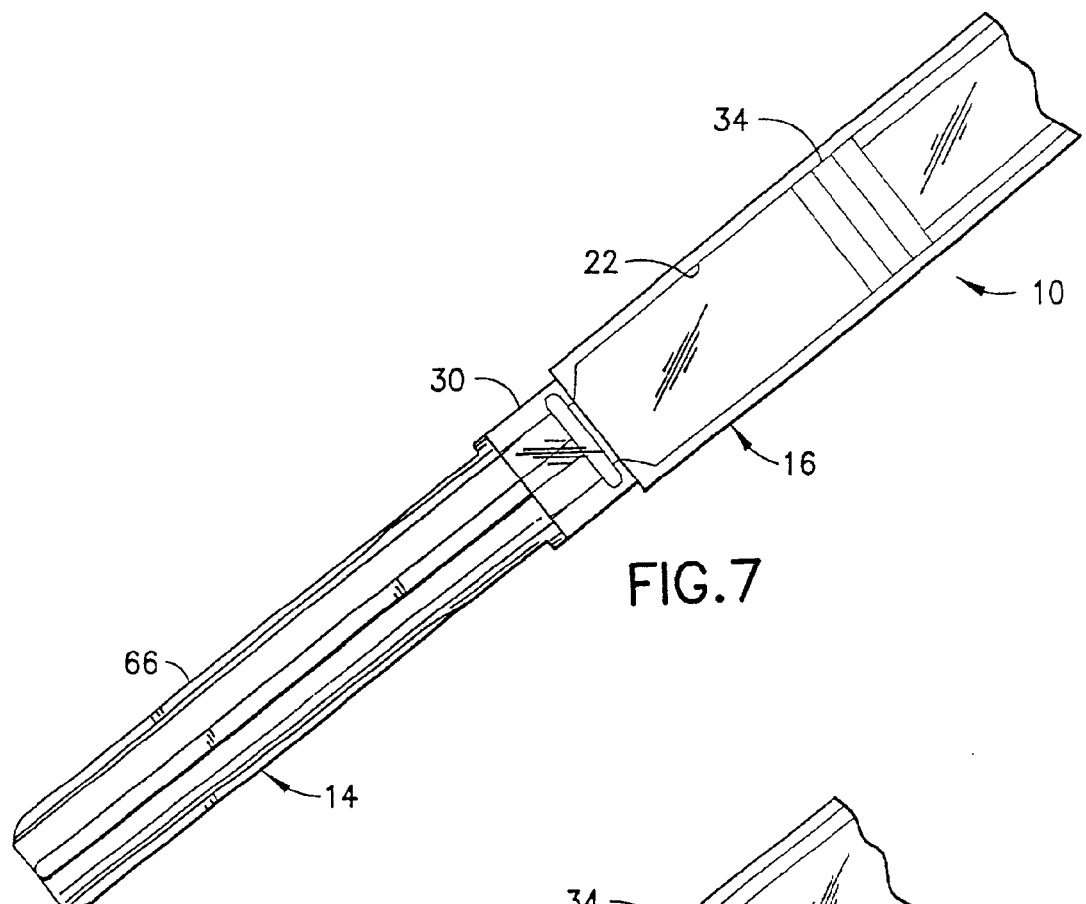
FIG. 7 is a side elevational view of the blunt cannula assembly of FIG. 4 mounted to the syringe of FIG. 2.
Figure 8:
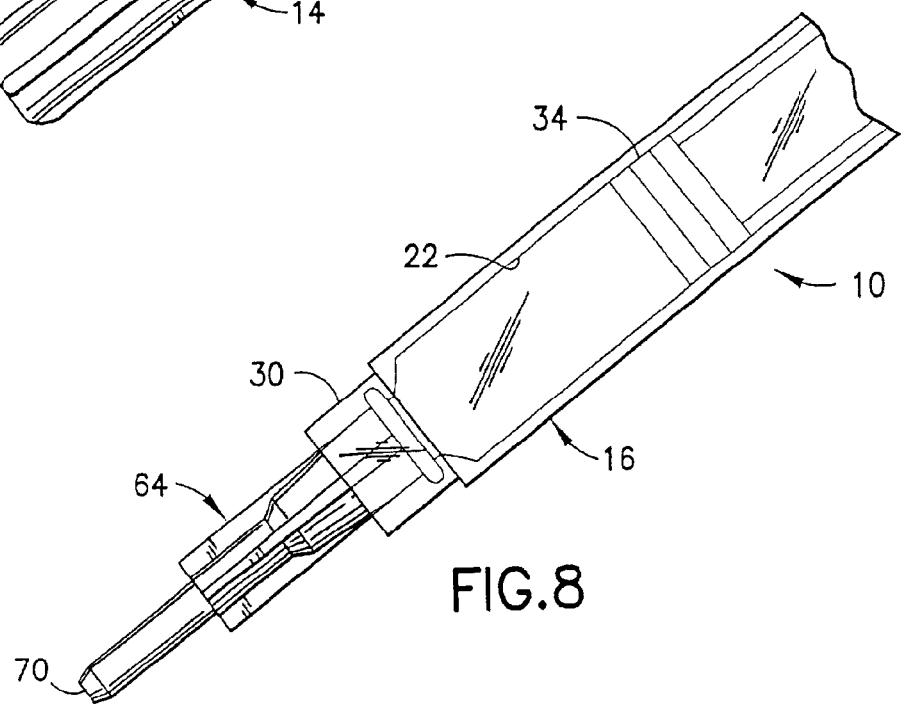
FIG. 8 is a side elevational view similar to FIG. 7, but showing the safety cap removed from the blunt cannula assembly.

Kit $K_1$ of FIG. 1 can be used with syringe 10 of FIG. 2 to perform diagnostic test on plasma of whole blood drawn from a patient. More particularly, syringe 10 is used in the conventional manner to draw a sample of blood from a patient. In this regard, syringe 10 can be employed with a conventional metallic needle cannula to directly access a blood vessel of a patient. Alternatively, Luer tip 26 of syringe body 16 can be mated with a fitting of an IV line that had previously been placed in communication with a blood vessel of a patient. Still further, Luer tip 26 of syringe body 16 can be placed in communication with a fitting which in turn is used with a blood collection set. With each of these options, proximal movement of plunger 34 draws blood into fluid receiving chamber 22 of syringe body 16. Syringe 10 then is separated from the source of blood, and blunt cannula assembly 14 is mounted to Luer tip 26. In particular, as shown in FIG. 7, blunt cannula assembly 14 may be engaged with Luer tip 26 of syringe body 16. Safety cap 66 of blunt cannula assembly 14 then is removed to expose blunt cannula 64 as shown in FIG. 8.

Figure 9:
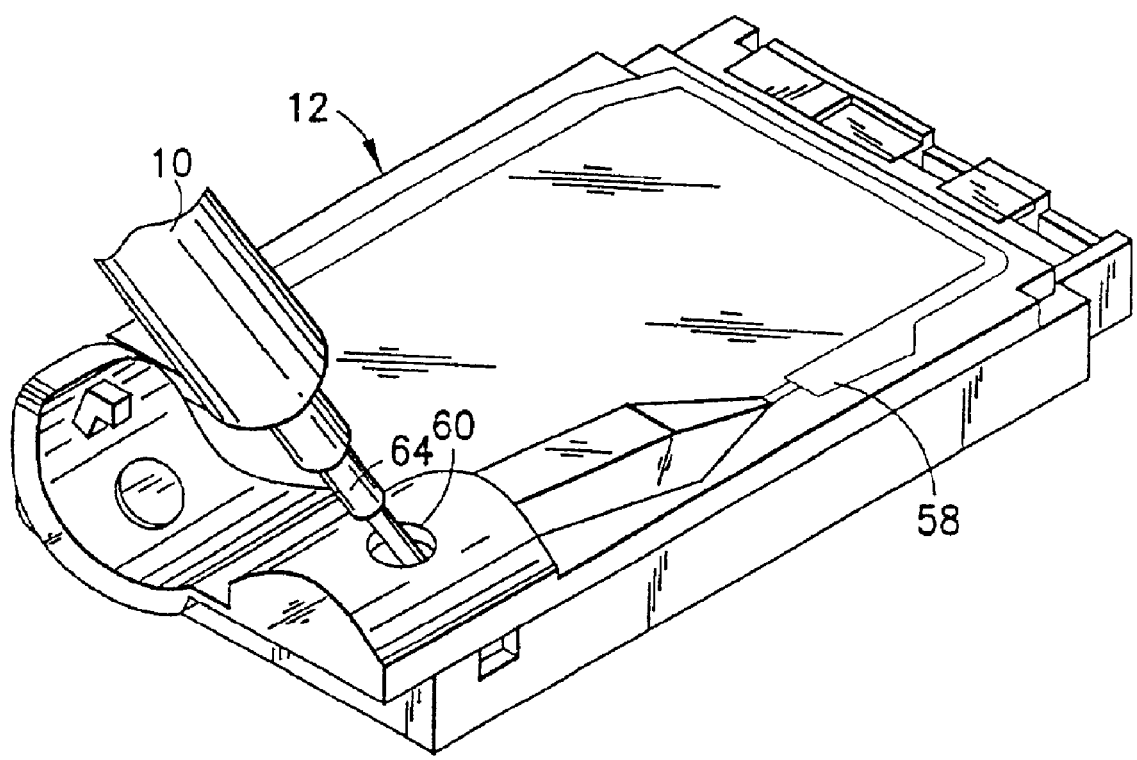
FIG. 9 is a perspective view of the syringe and blunt cannula assembly of FIG. 8 used with the testing cartridge of FIG. 3.

Distal end 70 of blunt cannula 64 then is inserted into entry port 60 of testing cartridge 12, as shown in FIG. 9. Plunger 34 is urged distally to direct a selected volume of the collected blood through filter 80A or dual filter 80B. Filter 80A or 80B separates cellular components from the whole blood that is urged from fluid receiving chamber 22 of syringe body 16. Thus forces of plunger 34 direct a plasma fluid into testing cartridge 12 for analysis. The overall yield of blunt cannula 64 may not be high due to premature clogging of the device. However, point-of-care testing cartridges require only a small volume (65 µl–110 µl) to complete an analysis of the collected specimen. Thus, filters 80A and 80B normally will be able to produce a sufficient volume of plasma for the testing cartridge prior to clogging. After a sufficient volume of plasma has been delivered to testing cartridge 12, syringe 10 and blunt cannula 64 are separated from testing cartridge 12. Entry port 60 then is closed, and testing cartridge 12 is presented to a portable clinical analyzer for diagnostic testing of the collected plasma specimen.

Figure 11:
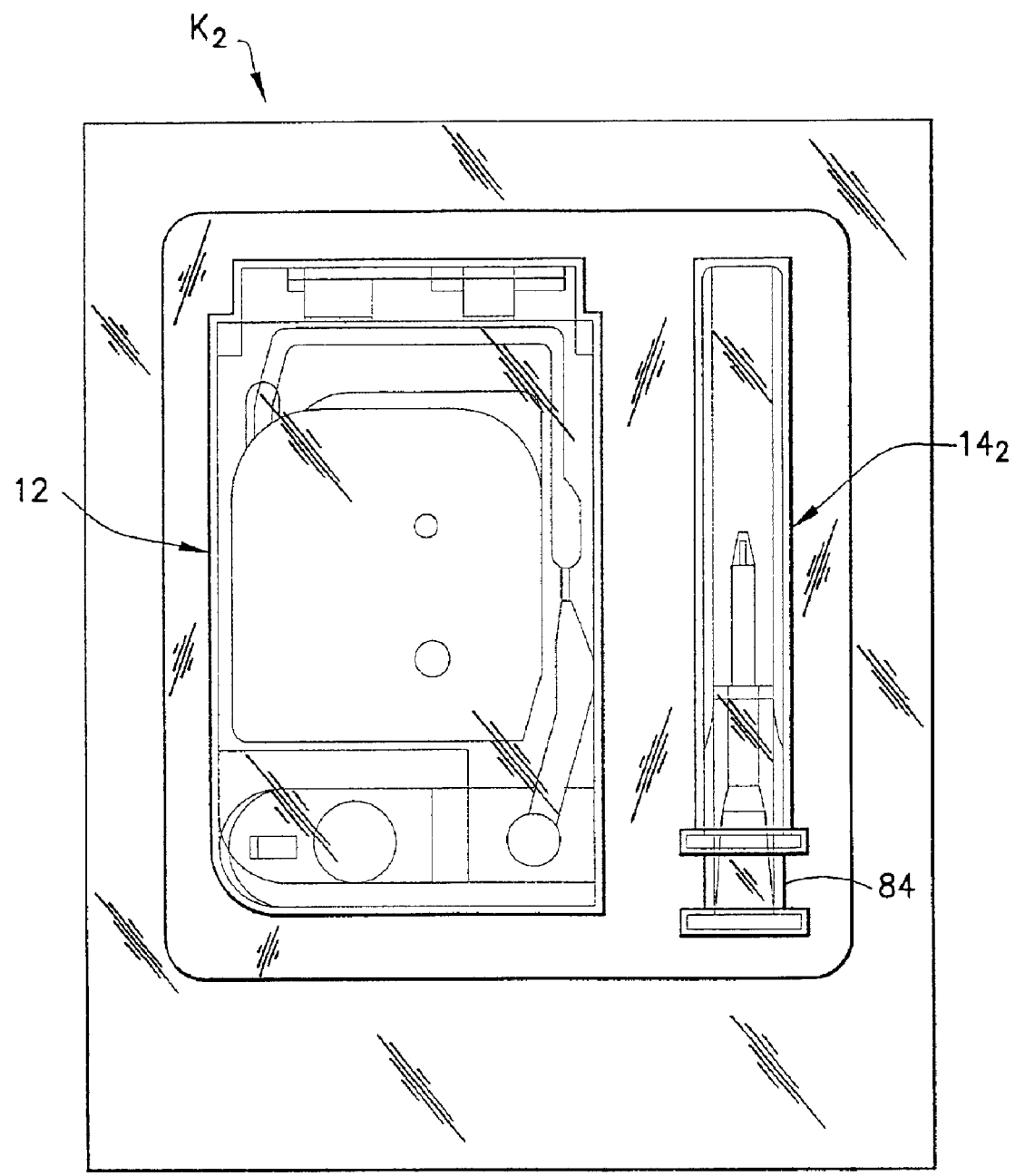
FIG. 11 is a top plan view of an alternate kit in accordance with the subject invention.
Figure 12:
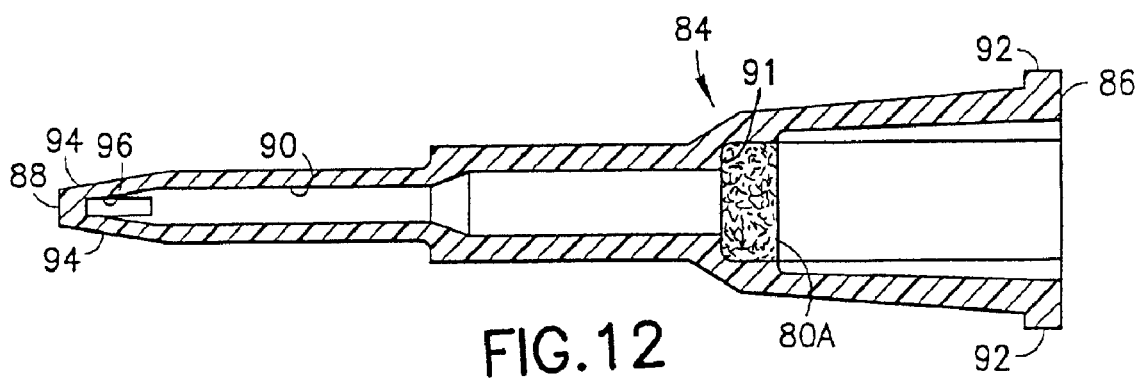
FIG. 12 is a longitudinal cross-sectional view of the blunt cannula shown in the kit of FIG. 11.

Kit $K_2$ of FIG. 11 includes a testing cartridge 12, identical to the testing cartridge 12 of kit $K_1$. Kit $K_2$ further includes a blunt cannula assembly $14_2$ similar to the blunt cannula assembly of Kit $K_1$. However, blunt cannula assembly $14_2$ of kit $K_2$ includes a blunt cannula 84 that is structurally somewhat different from blunt cannula 64 of kit $K_1$. More particularly, as shown in FIG. 12, blunt cannula 84 has a proximal end 86, a distal end 88 and a lumen 90 extending between the ends. Portions of lumen 90 adjacent proximal end 86 define a taper that substantially matches the tapered distal tip 26 on syringe body 16. Thus, tapered distal tip 26 of syringe body 16 can be placed in fluid-tight engagement with proximal end of lumen 90 in blunt cannula 84. Portions of lumen 90 adjacent distal end 88 are cross-sectionally much smaller than portions adjacent proximal end 86. Thus, a well defined step 91 is defined intermediate the length of lumen 90. Proximal end 86 of blunt cannula 84 is characterized further by a pair of diametrically opposite lugs 92 that are dimensioned and configured for engagement with threads 32 of Luer collar 30. Thus, lumen 90 through blunt cannula 84 can be placed in communication with passage 28 in tip 26 and fluid receiving chamber 24 of syringe body 16. Distal end 88 of blunt cannula 84 includes a narrow cylindrical tube that terminates with a pair of converging diametrically opposite triangular projections 94 that meet at a well defined tip. Triangular projections 94 are separated from one another by two oppositely facing ports 96.

Blunt cannula 84 further includes a filter 80A disposed at step 91 between the cross-sectionally large and small portions of lumen 90. Filter 80A is substantially identical to filter 80A of the first embodiment described above and illustrated in FIG. 5.

Figure 13:
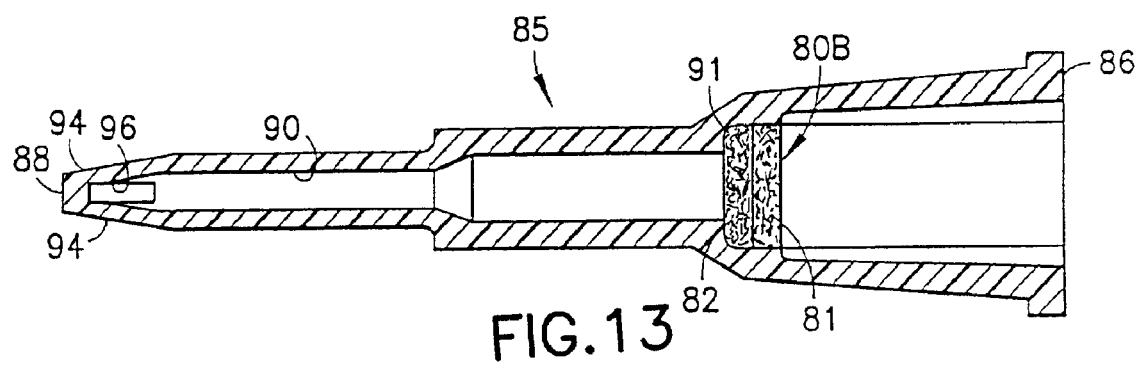
FIG. 13 is a longitudinal cross-sectional view similar to FIG. 12, but showing an alternate filter.

Blunt cannula 84 also may be used with dual filter 80B as shown in FIG. 13. Dual filter 80B is substantially identical to dual filter 80B described above and illustrated in FIG. 6 with reference to kit $K_1$.

Figure 10:
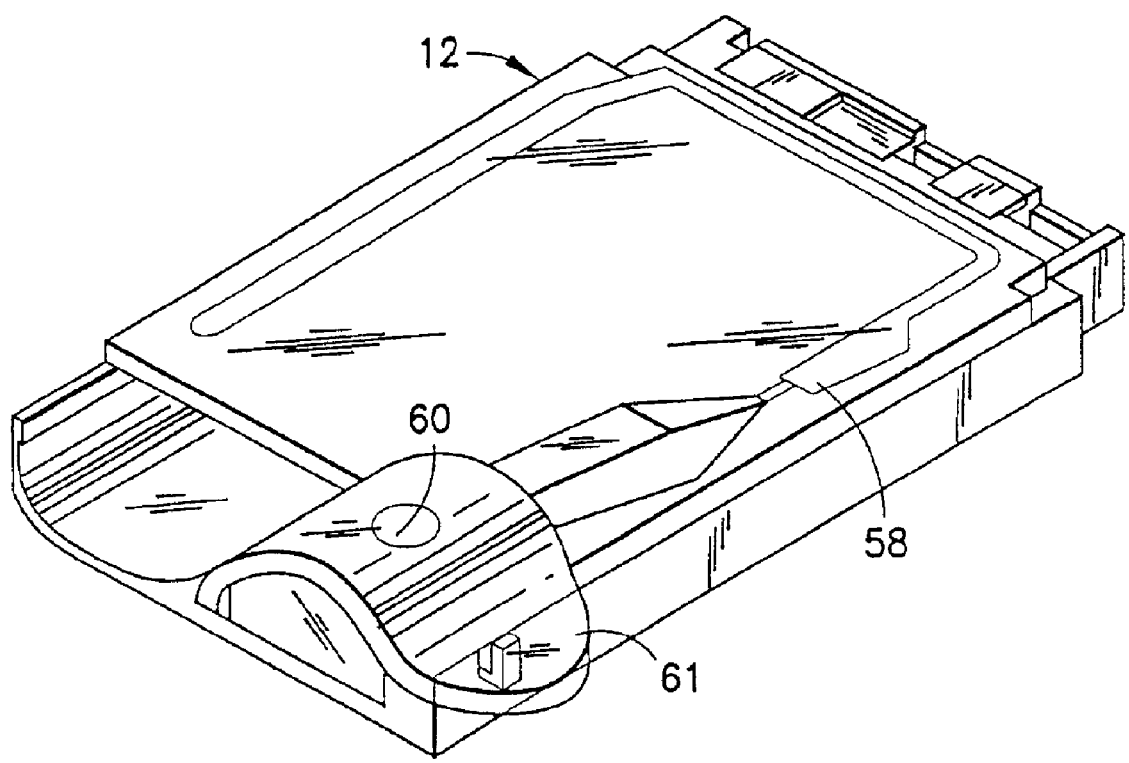
FIG. 10 is a perspective view of the testing cartridge after receiving a fluid specimen and prior to testing.
Figure 14:
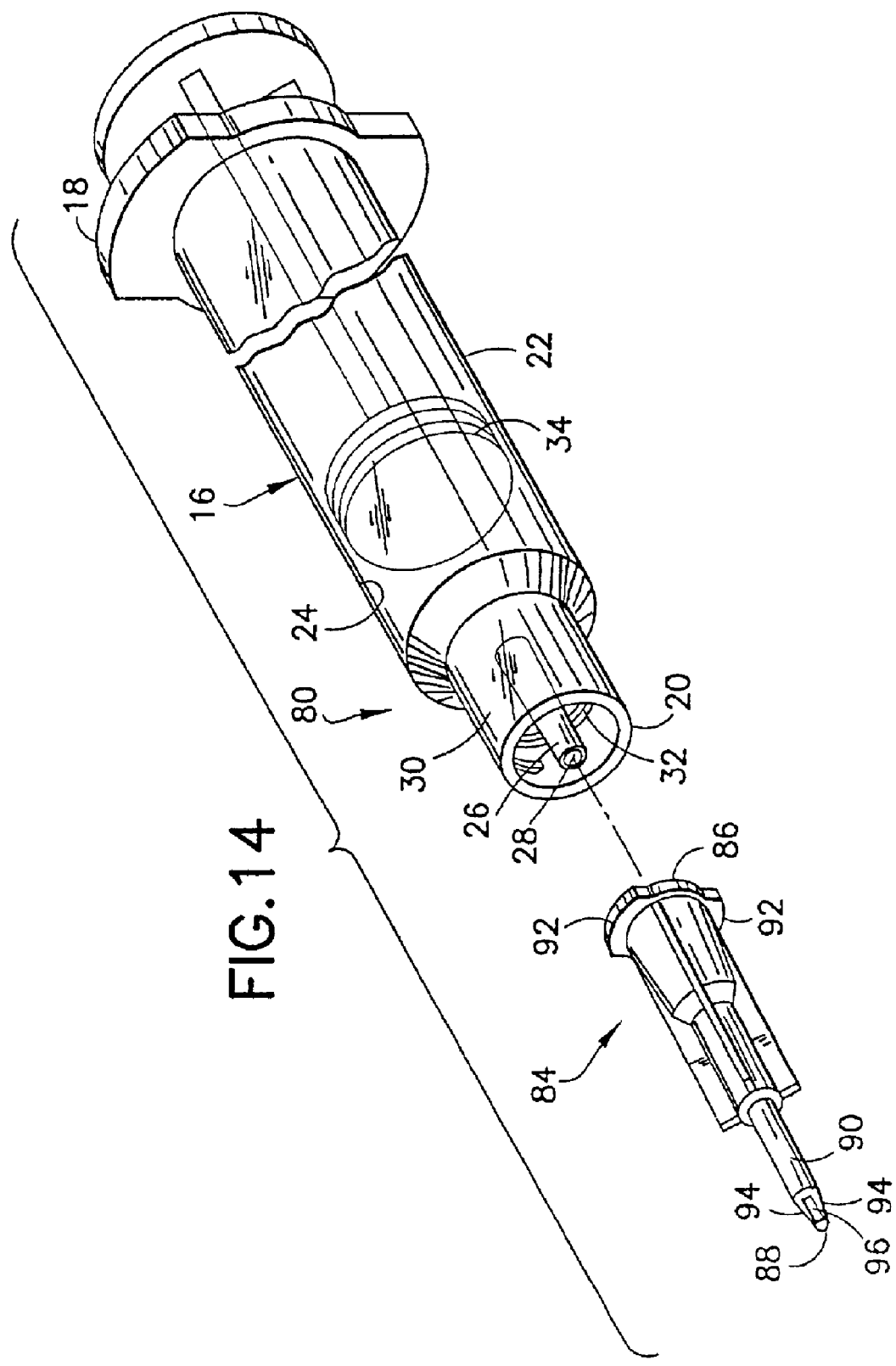
FIG. 14 is an exploded perspective view of the blunt cannula of FIG. 12 or 13 with the syringe of FIG. 2.

Kit $K_2$ is used exactly as kit $K_1$. More particularly, syringe 10 can be used to obtain a sample of blood from a patient. Blunt cannula 84 then can be mounted to syringe 10 as shown in FIG. 14. The assembly of blunt cannula 84 and syringe 10 then can be used exactly as the combination of syringe 10 with blunt cannula 64 as described above and illustrated in FIGS. 9–11.

What is claimed is:

1. A blunt cannula assembly comprising a cannula having a proximal end, a distal end and a lumen extending between said ends, said blunt cannula defining an annular step in the lumen and facing towards said proximal end, portions of said lumen adjacent said proximal end defining a tapered opening dimensioned and configured for fluid-tight mating with a Luer tip, a filter mounted in said lumen between said step and said tapered opening so that said Luer tip inserted into said tapered opening is opposed to said filter, portions of said blunt cannula adjacent said distal end having a pair of converging diametrically opposite triangular projections meeting at a well defined tip, said triangular projections being separated from one another by oppositely facing ports.

2. The blunt cannula of claim 1, wherein said filter comprises a dual filter having first and second filter layers adjacent to one another.

3. The blunt cannula of claim 2, wherein said filter layers are connected to one another.

4. The blunt cannula of claim 1, wherein said filter has a pore size between 0.2–5.0 microns.

5. The blunt cannula of claim 1, wherein said filter is selected from the group consisting of glass fibers, glass wool, nylon and ceramic fibers.

6. The blunt cannula of claim 1, wherein said proximal end of said blunt cannula comprises a pair of diametrically opposite lugs configured for mating with a Luer collar.

7. The blunt cannula of claim 1, wherein said filter comprises an anticoagulant for preventing clotting of a selected fluid material that passes through said filter.

* * * * *